(12) United States Patent
Patterson (10) Patent No.: US 8,390,304 B2
(45) Date of Patent: Mar. 5, 2013

(54) ELECTRICAL RESONANCE DETECTION OF PARTICLES AND ANALYTES IN MICROFLUIDIC CHANNELS

(75) Inventor: Donald A Patterson, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 779 days.

(21) Appl. No.: 12/388,904

(22) Filed: Feb. 19, 2009

(65) Prior Publication Data

US 2009/0212788 A1 Aug. 27, 2009

Related U.S. Application Data

(60) Provisional application No. 61/066,762, filed on Feb. 22, 2008.

(51) Int. Cl.
*G01R 27/08* (2006.01)
*C12Q 1/00* (2006.01)

(52) U.S. Cl. .................................... 324/691
(58) Field of Classification Search .......... 324/691
See application file for complete search history.

(56) References Cited

U.S. PATENT DOCUMENTS

| | | | | |
|---|---|---|---|---|
| 6,339,335 | B1 * | 1/2002 | Froger et al. | 324/636 |
| 2002/0053104 | A1 * | 5/2002 | Rump et al. | 4/313 |
| 2004/0036487 | A1 * | 2/2004 | Heremans et al. | 324/698 |
| 2004/0160162 | A1 * | 8/2004 | Eden et al. | 313/495 |
| 2005/0279855 | A1 * | 12/2005 | Baker et al. | 239/71 |
| 2008/0071487 | A1 * | 3/2008 | Zeng et al. | 702/65 |
| 2009/0308155 | A1 * | 12/2009 | Zhang | 73/335.02 |

OTHER PUBLICATIONS

D. E. Johnson and C. G. Enke, Bipolar Pulse Technique for Fast Conductance Measurements, Analytical Chemistry, vol. 42, No. 3, Mar. 1970, p. 329-335.
Adams, A.A. et al., "Highly Efficient Circulating Tumor Cell Isolation from Whole Blood and Label-Free Enumeration Using Polymer-Based Microfluidics with an Integrated Conductivity Sensor," J. Am. Chem. Soc., vol. 130, pp. 8633-8641 (2008).

(Continued)

*Primary Examiner* — Jeff Natalini
(74) *Attorney, Agent, or Firm* — John H. Runnels; Bonnie J. Davis (57) ABSTRACT

A conductivity counter and method of determining conductivity of a fluid sample are disclosed. The counter is suitable for high-speed, accurate counting of discrete events or items, such as cancer cells, passing through a fluid sample cell. A variable frequency current source is used to supply an excitation current to a sample cell connected in parallel with an inductance or the electrical equivalence of an inductance. This configuration can be accurately modeled as a parallel RLC circuit when the system is operated at a stable frequency. The current source frequency is tuned to the resonance frequency of the equivalent RLC circuit, which effectively eliminates the capacitive and inductive components of the impedance, leaving only purely resistive components. The output of the equivalent RLC circuit is connected to a high input impedance buffer amplifier and then to a phase sensitive detector, which detects the phase shift resulting from the equivalent RLC circuit. The output is filtered and a differencing amplifier is used to zero out the output signal due to the system components and the sample cell buffer solution prior to taking active readings. The remaining output signal is due to perturbations in the fluid sample, such as passing cancer cells. This output is sent to a high-gain output amplifier and then supplied to a suitable signal processing device or system, such as a computer.

23 Claims, 11 Drawing Sheets

OTHER PUBLICATIONS

Adams, A.A. et al., "Highly Efficient Circulating Tumor Cell Isolation from Whole Blood and Label-Free Enumeration Using Polymer-Based Microfluidics with an Integrated Conductivity Sensor," J. Am. Chem. Soc., vol. 130, pp. S1-S16 (2008) Supporting Information.

Zheng, S. et al., "Resonance Induced Impedance Sensing of Human Blood Cells," Proceedings of the 14th International Conference on Solid-State Sensors, Actuators and Microsystems (Transducers '07), Lyon, France, pp. 1741-1744 (2007).

* cited by examiner

ELECTRICAL RESONANCE DETECTION OF PARTICLES AND ANALYTES IN MICROFLUIDIC CHANNELS

PRIORITY CLAIM UNDER 35 U.S.C. 119(e)

This application claims the benefit of U.S. Provisional Application No. 61/066,762, filed on Feb. 22, 2008.

This invention was made with government support under EPS0346411, awarded by the National Science Foundation. The government has certain rights in the invention.

FIELD OF THE INVENTION

The invention relates to an apparatus for making fast, accurate conductivity measurements of a fluid sample, and a method of calibrating a conductivity measurement apparatus and making conductivity measurements.

BACKGROUND OF THE INVENTION

Various techniques have been used to count events or items contained in fluid samples. Visual counting, using magnification and highly specialized recognition software, has been used. Conductivity counting also has been used to detect bands of DNA separated via electrophoresis. A bipolar pulse method has been used for such conductivity measurements. This method uses a bipolar pulse signal and makes use of the property that the sample cell parallel capacitance is orders of magnitude smaller than that of the series double-layer capacitance. This method is described in *Bipolar Pulse Technique for Fast Conductance Measurements*, by D. E. Johnson and C. G. Enke, published in Analytical Chemistry, Vol. 42, No. 3, March 1970, and hereby incorporated by reference into this application.

The bipolar pulse method provides a reasonably fast and accurate method of measuring conductivity of a fluid sample cell. The problem identified and discussed in the article cited above is the existence of two distinct capacitances exhibited by a typical fluid sample cell. In a such a cell, an electrolyte buffer solution is used as the base or background material. The samples of interest are then placed in this buffer solution. A pair of electrodes are positioned at opposite sides of the sample cell, and the conductivity across the electrodes is measured. As an item of interest (i.e., an article with conductivity measurably different from that of the buffer solution) passes the electrodes, the device detects the conductivity change. Unfortunately, the existence of capacitance due to the cell itself leads to inaccuracies in the measurements.

The Johnson and Enke article notes that a fluid sample cell exhibits a capacitance in series with the resistance of the sample and a capacitance in parallel with the cell resistance. The first capacitance is identified as a double-layer capacitance ($C_d$), and the latter as the parallel cell capacitance ($C_p$). In the bipolar pulse method, square wave pulses are used with inverse polarity, and the measurement is made at the trailing end of the second pulse. This approach results in a charging/discharging process for the parallel cell capacitance ($C_p$), which is essentially complete by the time the measurement is taken. In this manner, the bipolar pulse method effectively eliminates the influence of the two cell capacitances, and produces conductivity measurements proportional to changes in the conductivity of the sample.

Though the bipolar pulse method is reasonable fast, it is not without its share of problems. Two pulses are required for a single measurement, and the pulses must be long enough to allow for the parallel cell capacitance ($C_p$) to fully charge yet short enough to prevent the double-layer capacitance ($C_d$) from significantly charging and limiting the current before it is sampled. Therefore, it is necessary to have some prior knowledge of these capacitor values in order to select the most appropriate pulse lengths. This method can take measurements up to every 40 µsec, based on use of 20 µsec pulses.

The bipolar pulse method is also dependant upon the geometry of the sample cell. $C_d$ must be greater than $C_p$ in order for the technique to work. When the sample cell is very small, this relationship between the capacitors is no longer true. It has been found that for individual cell counts, a sample tube diameter of approximately 50 microns is advantageous. This size tube is small enough to isolate individual cells without them clogging in the tube. This small sample tube size, however, does not work well with the bipolar pulse method because the two cell capacitances ($C_d$ and $C_p$) are within less than one order of magnitude of each other. In addition, the currents thru the cell must be connected to the inverting input of an opamp to be converted to a voltage. Unless the opamp is in close proximity to the cell, the stray capacitance from the inverting input to ground can cause severe ringing in the bipolar pulse. Finally, the experiments in micro-channels using this technique tend to have a low signal to noise ratio, and it is difficult to measure less than 2% changes in conductance.

An improved apparatus and method, therefore, is needed for performing fast, accurate conductivity measurements of a fluid sample. This apparatus and method would be of particular utility for counting individual cells, such as cancer cells, contained in a fluid sample. A fast count rate is needed. A good signal to noise ratio is also needed to ensure that individual cells are not missed. To accomplish this result, the apparatus and method must effectively deal with the capacitive effects of the sample cell. The bipolar pulse method is one way to doing this, but it does not work well with small sample cells and small conductivity changes. A new design is needed. The present invention is such a design.

SUMMARY OF THE INVENTION

The present invention utilizes an equivalent parallel RLC circuit to effectively eliminate the capacitances of the sample cell. By operating such a circuit at its resonance frequency, the impedance of the reactive components (i.e., the capacitive and inductive components) cancel each other out, leaving only the purely resistive components. The resistance (or conductivity) remaining is due to the circuit components, the sample cell components, and the fluid sample. Once the circuit is operating at resonance frequency, the output signal caused by the background resistance components (i.e., those of the circuit, cell, and buffer solution) can be eliminated. The output signal is thus zeroed out prior to taking actual measurements, which allows use of a high-gain output amplifier, thus enhancing the signal to noise ratio of the apparatus.

In a preferred embodiment, the present invention has a variable frequency, high output impedance, current source; a sample cell having both resistive and capacitive characteristics electrically connected to the current source; a low-loss, low-noise inductance connected to the current source and in parallel with the sample cell, such that the sample cell and inductance effectively form a parallel RLC circuit; a high input impedance buffer amplifier connected to the output of the parallel RLC circuit; a phase sensitive detector connected to the output of the high input impedance buffer amplifier; a background conductivity offset circuit; a differencing amplifier with a first input connected to the output of the phase sensitive detector and a second input connected to the output of the background conductivity offset circuit; and, a high gain output amplifier connected to the output of the differencing amplifier.

In another preferred embodiment, the present invention includes the steps of applying a variable frequency current source to a parallel RLC circuit; detecting the voltage amplitude and phase shift of the output of the parallel RLC circuit; varying the frequency of the current source while monitoring the voltage amplitude of the output of the parallel RLC circuit to determine the resonance frequency of the parallel RLC circuit, which is indicated by the frequency at which the circuit's output voltage has maximum amplitude; fixing the current source frequency at the resonance frequency of the parallel RLC circuit; zeroing out the output signal resulting from measurement of a buffer solution alone, using a differencing amplifier and a background solution offset circuit; and, amplifying the output signal resulting from changes in the conductivity of the sample fluid.

DETAILED DESCRIPTION OF PREFERRED EMBODIMENTS OF THE INVENTION

Figure 1:
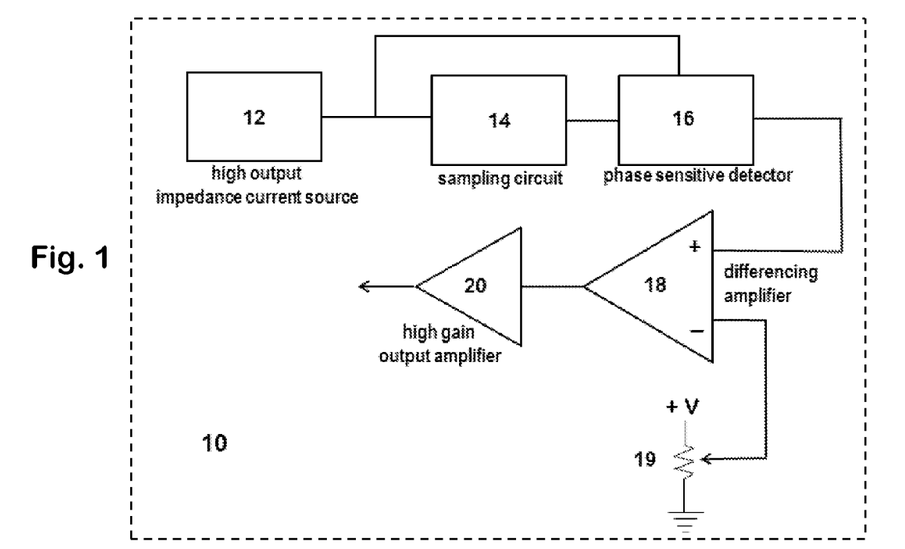
FIG. 1 is a block diagram of a preferred embodiment of the present invention.

A conductivity counter apparatus 10 of the present invention is shown in block diagram form in FIG. 1. The first block represents a variable frequency, high output impedance current source 12, which supplies an excitation current to the sampling circuit 14. It is important that the sampling circuit 14 be effectively isolated from impedance effects of other parts of the circuit. For this reason, the excitation circuit should have high output impedance. The current source 12 is designed to provide this characteristic. It is also necessary that the current source 12 be tunable, that is, have a variable frequency that may be swept through a fairly broad range of frequencies. This capability is needed to find the resonance frequency of the equivalent RLC circuit, as described below.

The sampling circuit 14 is isolated from downstream impedance effects by using an output buffer amplifier having a high input impedance. This buffer is part of the sampling circuit block 14, as illustrated in FIG. 1. The output of the sampling circuit 14 is connected to a phase sensitive detector and filter block 16. The equivalent RLC circuit produces a phase shift between the input and output of the sampling circuit 14. The output of the current source 12, therefore, is connected to the phase sensitive detector 16, which then senses differences in phase caused by the reactive components of the sampling circuit 14.

The output of the phase sensitive detector and filter block 16 is connected to one input of a differencing amplifier 18. The other input of the differencing amplifier 18 is connected to a potentiometer 19, which is used to null the output of the differencing amplifier 18 when only a buffer is present in the sample cell. When this is done, future changes in the conductivity of the sample (i.e., changes due to the presences of items of interest) will account for all or most of the output signal from the differencing amplifier 18.

The output signal from the differencing amplifier 18 is amplified by a high-gain output amplifier 20, which increases the signal amplitude. It is important to null the output due to the buffer alone, so that the signals due to the items of interest will produce the maximum signal perturbations possible. The high-gain output amplifier 20 allows for much greater ability to detect discrete events or items being counted. Each of the blocks of the invention illustrated in FIG. 1 will be described in more detail below.

Figure 2:
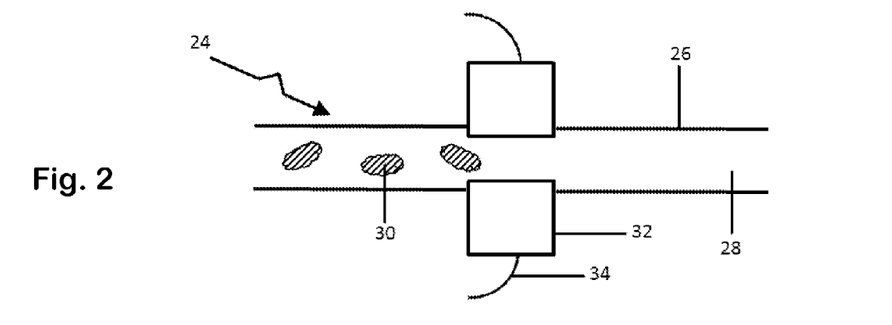
FIG. 2 is a schematic diagram of a sample cell used to count individual cells.

FIG. 2 shows, in a schematic form, a typical sample cell configuration. The sample cell 24 is shown in cross-section. It includes an outer shell or tube 26 and inner channel, which typically is cylindrical or rectangular in cross section to facilitate passage of materials. A buffer solution 28 fills the tube 26. In this example, individual cells 30 (e.g., cancer cells) are introduced into the buffer solution 28 that is moving through the cell 24. A pair of electrodes 32 are located on opposite sides of the tube 26, and are connected to the rest of the circuit via electrical leads 34. As a cancer cell 30 moves past the electrodes 32, the conductivity changes. This is the basic configuration of the sample cell 24.

The construction of the sample cell is well known within the art, as tubular sample cells of the type used with the current invention are in widespread use. The sample cell may have a generally circular, oval, square, or rectangular cross-section, and should be of sufficient length to allow for the introduction of the test materials a reasonable distance away from the measuring electrodes. The sample cell also may be constructed as part of an integrated circuit, with conductive polymer electrodes fabricated as part of the intergrated circuit construction. This approach is advantageous because of the small channel size (e.g., approximately 50 microns in a preferred embodiment) used with the current invention.

Figure 3:
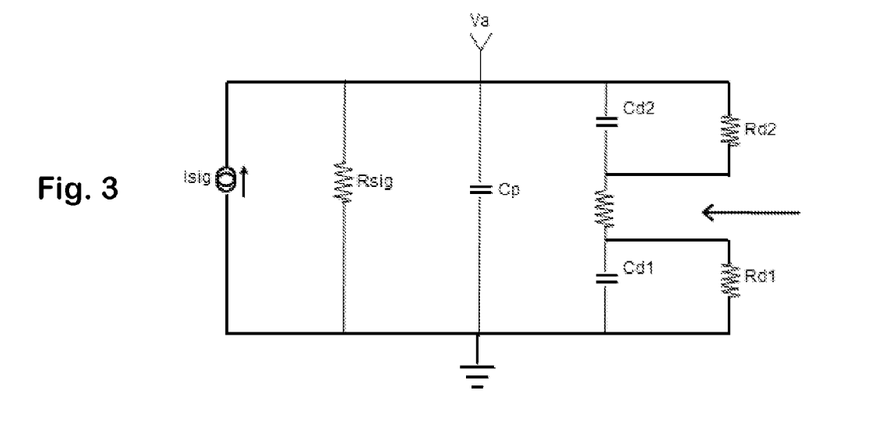
FIG. 3 is an electrical schematic diagram of the electrical equivalent of the sample cell shown in FIG. 2.

The electrical circuit equivalent (i.e., a model) of the sample cell 24 is illustrated schematically in FIG. 3. A current source ($I_{sig}$) supplies the sample cell. The current source circuit has an output impedance ($R_{sig}$), which is shown in parallel with the sample cell components. The sample cell is modeled as a group of resistors and capacitors. In a preferred embodiment, the sample cell tube 26 has a diameter of approximately 50 microns and the electrodes are about 75 microns in length (i.e., as measured along the axis of the sample tube 26). These dimensions have produced good results in the lab.

The sample resistance (or conductivity) is identified as $R_s$ and is shown at the center of the right-most part of the circuit. This is the parameter of interest, the one that must be isolated to obtain the most accurate readings. The electrodes have both capacitive and resistive characteristics, and these are shown above and below the sample resistance in the circuit. The electrode double layer capacitance of the first electrode ($C_{d1}$) and the resistance of the first electrode ($R_{d1}$) are shown below the sample resistance ($R_s$). The capacitance and resistance of the other electrode ($C_{d2}$ and $R_{d2}$) are shown above the sample resistance ($R_s$). The important point is that these resistance and capacitance contributions are in series with the sample resistance ($R_s$). The parallel cell capacitance ($C_p$) is shown in parallel with the sample resistance ($R_s$) in FIG. 3.

Figure 4:
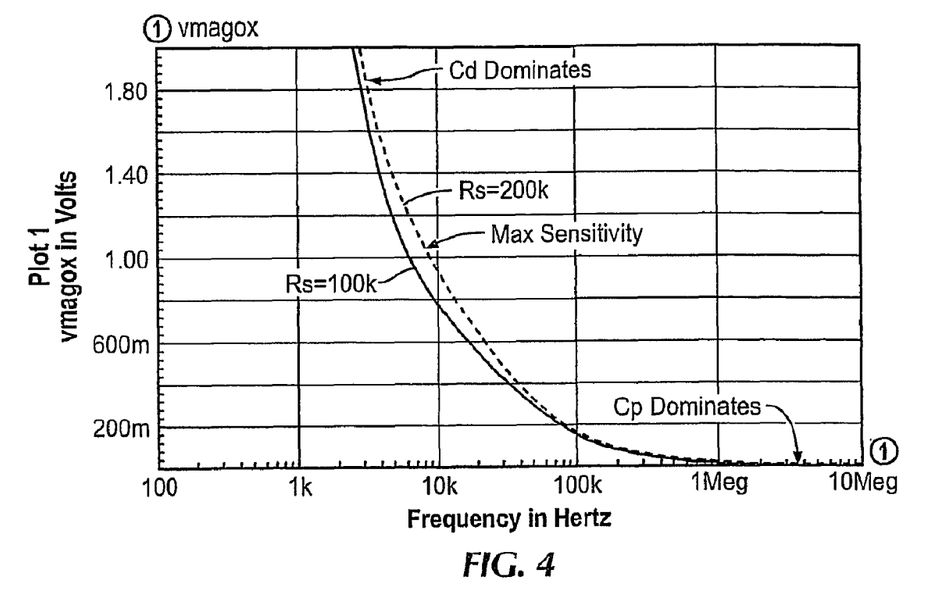
FIG. 4 is a graph showing results produced using the electrical circuit configuration shown in FIG. 3.

Using SPICE, the simulated results of cell conductivity made using the arrangement shown in FIG. 3 are shown in FIG. 4. The two lines shown represent sample cell resistances of 100KΩ and 200KΩ. The curve that diverges to the right represents the 200KΩ results. A number of important results are illustrated in FIG. 4.

First, and perhaps most importantly, the separation of the two curves is highly dependent upon frequency. At a frequency of about 10 KHz, maximum sensitivity is obtained. The difference, however, between these two samples under these conditions is only about 0.30. That is only about ⅓ the magnitude of the difference in the actual sample resistances. Not only are the results frequency dependant, but the signal to noise ratio is not very good.

At low frequencies, the electrode double layer capacitance effects dominate the results because these capacitance effects are in series with the sample resistance. As the frequency decreases, the impedance created by these capacitances increases and dominates the resistance of the actual sample. At high frequencies, on the other hand, the parallel cell capacitance dominates because it is in parallel with the sample resistance. As the frequency rises, the impedance of the parallel cell capacitance decreases, and eventually becomes effectively a short circuit, shorting out the sample.

Figure 5:
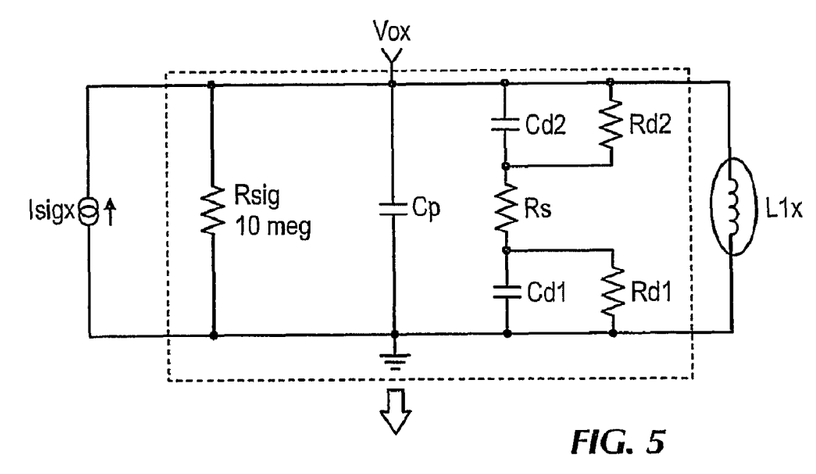
FIG. 5 is an electrical schematic diagram showing the addition of an inductor to the circuit of FIG. 3.
Figure 6:
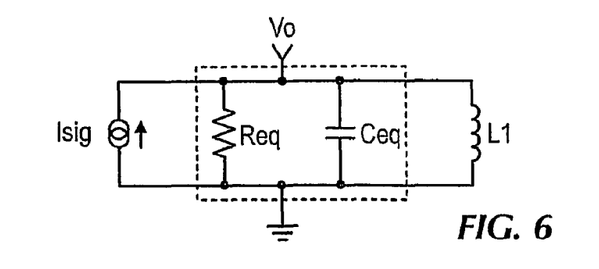
FIG. 6 is an electrical schematic diagram showing an approximation of the circuit of FIG. 5 under certain conditions.

The solution utilized in the present invention is illustrated in FIGS. 5 and 6. FIG. 5 shows the same equivalent circuit schematic from FIG. 3, but with an additional inductor in parallel with the other components. This change results in an RLC circuit, which creates the potential to tune out the reactive impedance effects by operating the circuit at the resonance frequency. When the circuit components have relatively constant values and when the circuit is operated at a stable (i.e., nonfluctuating) frequency, the circuit for FIG. 5 may be approximated by the circuit of FIG. 6. All the cell capacitance effects are modeled as a single equivalent capacitance ($C_{eq}$) in parallel with an equivalent cell resistance ($R_{eq}$). This simplified model of the circuit results in an equivalent parallel RLC circuit, a design often referred to as a tank circuit.

The sample cell may be modeled as an electrical circuit having a resistance in parallel with a capacitance, as shown within the dashed lines of FIG. 6. This model is sufficiently accurate over a fairly broad range of frequencies, though the actual parameter values (i.e., $R_{eq}$ and $C_{eq}$) would, at least in theory, have to be recalculated for each discrete frequency. This is a theoretical, not practical, concern because the actual values of these equivalent components need not ever be determined during operation of the invention. The important point is that the sample cell may be accurately modeled as a parallel RC circuit, which can be readily converted to an RLC tank circuit by the addition of an inductance in parallel with the sample cell. The parallel RC model shown within the dashed lines in FIG. 6 holds for frequencies within the range of interest.

The operation of the equivalent circuit shown in FIG. 6 is straightforward. When the current source is operated at the resonance frequency of the equivalent RLC circuit, the capacitance and inductance effectively cancel each other out, leaving only the equivalent resistance ($R_{eq}$). This resistance does not result from the sample alone. It is a composite of the sample resistance and other resistances, as explained above. But only the resistance due to the actual sample will vary in a significant manner, and thus if the output signal due to the background is nulled, the result is a signal due almost entirely to variations in the resistance (i.e., the conductivity) of the sample. That is the desired result.

Getting to that result, however, is not so easy. First, the current source must be tunable. It must allow for a range of frequency tuning that allows the frequency to be set to the resonance frequency of the equivalent RLC circuit. It is not easy or very practical to accurately determine the equivalent capacitance of the cell in advance, so only by sweeping the frequency of the current source is it possible to fix the resonance frequency.

To facilitate the setting of the resonance frequency, and to better detect output signals, a phase sensitive detector is used. This detector, which was illustrated by block 16 in FIG. 1, compares the phase of the input and output of the sampling circuit. When the circuit is in resonance, there should be a 0° phase shift between the input and output. By monitoring the output of the phase sensitive detector while sweeping through the frequency range of the current source, it is possible to accurately determine the resonance frequency for the actual apparatus at the time a sample is to be taken. Once the resonance frequency is determined, the current source is set at that frequency and is not altered during the measurement process (i.e., the frequency is stable) unless there is reason to believe the characteristics of the system have changed (e.g., if a different buffer solution is introduced into the sample cell, or if a different cell is substituted, or other components are changed).

The frequency selection aspect of the current invention is highly advantageous. It results in a very high signal to noise ratio, because the output measurements are always taken at resonance frequency, which produces the minimum phase shift and maximum amplitude variation. It allows for accurate and simple calibration of the apparatus without any prior knowledge of the characteristics of the sample cell, buffer solution, or other variable parameters. Once the resonance frequency is set, measurements may be taken without need for further recalibration of the apparatus. These are all important advantages over existing systems.

Figure 7:
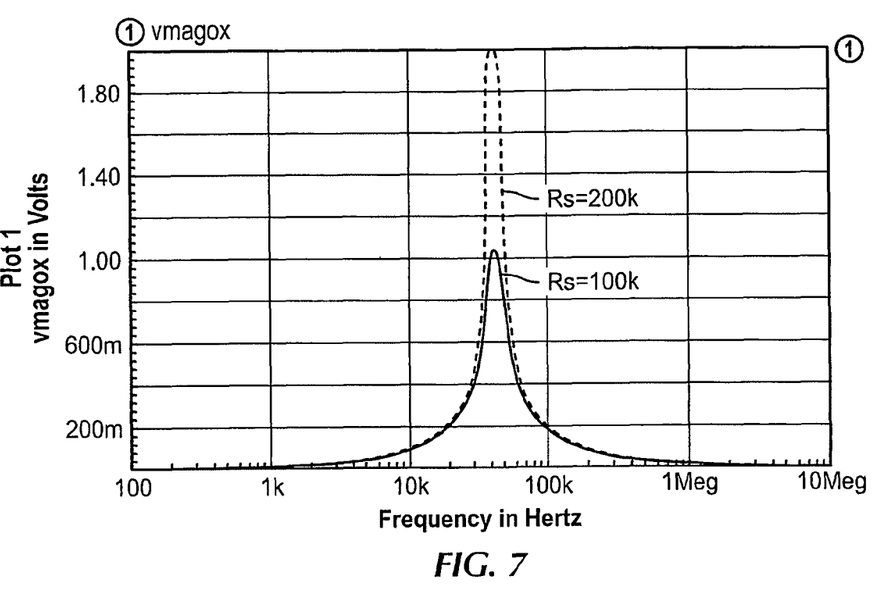
FIG. 7 is a graph showing results produced using the electrical circuit configuration shown in FIGS. 5 and 6.

FIG. 7 illustrates the results. Using the same sample resistances of 100KΩ and 200KΩ, a very different output is obtained, as compared to the graph shown in FIG. 4. A very clear spike is produced for both samples, allowing for accurate counting. In addition, the spike for the 200KΩ sample is approximately twice as high as that of the 100KΩ sample. The signal to noise ratio is quite good with this apparatus. The specific frequency at which the spikes occur will vary (i.e., the resonance frequency will vary), but the general nature of the spikes illustrated in FIG. 7 is a repeatable result obtained through use of the present invention. Accurate counts of cancer cells were obtained in numerous test runs using the invention.

There is, however, another challenge posed by this design. It requires use of an inductor, or the electrical equivalence of an inductor. This requirement is referred to at times in this description as an inductance, which refers generically to any component or circuit that creates the electrical equivalent of an inductor. To obtain a resonance frequency in a usable range—that is, within a range achievable with a variable frequency current source—a relatively large inductance is needed. For example, it was determined that an inductance in the range of 100-200 mH is needed for typical sample cell configurations. That would be a large inductor. And that poses problems.

Large inductors are typically expensive, physically large (i.e., relative to the other electrical components of this apparatus), have relatively high losses, and aren't easily fabricated in ICs. All of these characteristics make typical inductors poorly suited for the present invention. Indeed, the lossy nature of many large inductors would potentially eliminate the important signal to noise ratios otherwise obtainable with the present invention.

An alternative used in a preferred embodiment is a gyrator configured to simulate an inductor. Over 50 years ago, it was discovered that a pair of operational amplifiers with a series of resistors and a single capacitor can be used to create a reactive impedance inverter, or a gyrator, as the circuit has been called. This requires a number of components, but each component is small, inexpensive, has minimal losses, and easily fabricated into modern ICs. In other words, a gyrator with a capacitor can be used to simulate a relatively large inductor, and can do so in a way that avoids the problems noted above.

Figure 8:
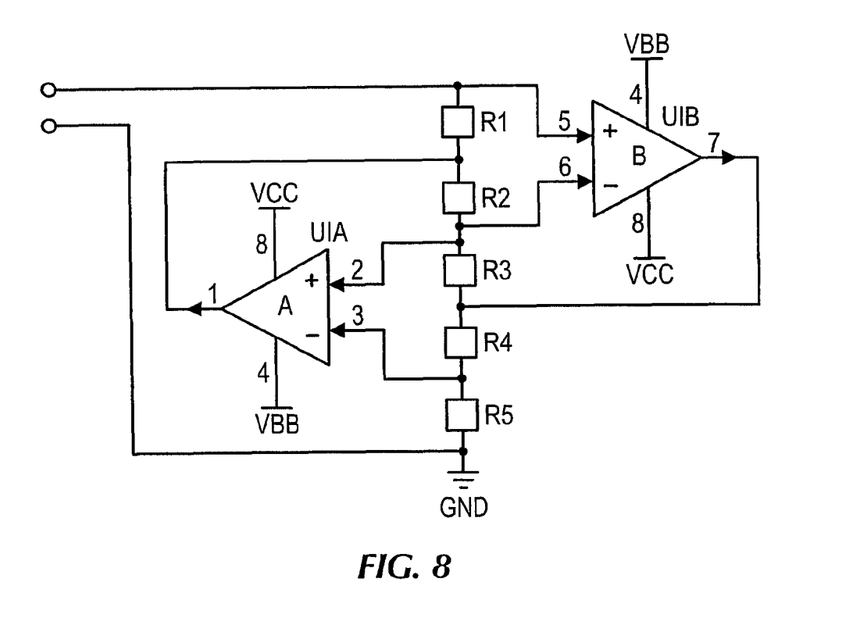
FIG. 8 is an electrical schematic diagram of a gyrator simulating an inductor.

FIG. 8 shows such a gyrator. It consists of four resistors and one capacitor and a pair of operational amplifiers. The operation of a gyrator is well-known in the art, as such circuits have been used in the past in filters and other devices. The result of the gyrator shown in FIG. 8 is an input impedance defined by the following equation: $Z_{in}=R_1*R_3*R_5/R_2*Z_4$. If all the resistors have the same value, the input impedance becomes: $Z_{in}=R^2/Z_4$. The input impedance is proportional to the inverse of the impedance of the capacitor in the gyrator, and thus, the gyrator effectively acts like an inductor.

In a preferred embodiment of the present invention, a gyrator is used to simulate a relatively large inductor. The gyrator is placed in parallel with the sample cell, which results in an equivalent parallel RLC circuit. This circuit is then tuned to its resonance frequency to maximize the sensitivity and accuracy of the apparatus.

The present invention also may use a true inductor, though traditional inductors may not work well for the reasons stated above. Technical developments in the design of inductors have improved the performance of these components. For example, integrated circuit design techniques now allow for the creation of relatively low-noise inductors on silicon-based integrated circuits. A 3-D high-Q coil inductor consisting of two turns of 5 micron thick and 50 micron wide copper traces that are electroplated around an alumina core is described in the following paper: *A Low-Noise RF Voltage-Controlled Oscillator Using On-Chip High-Q Three Dimensional Coil Inductor and Micromachined Variable Capacitor*, Darrin J. Young, et al., Solid-State Sensor and Actuator Workshop; Hilton Head Island, S.C., Jun. 8-11, 1998. The contents of this paper are hereby incorporated by reference into this application. An IC inductor of the type disclosed in this paper, and other advanced inductor designs having high-Q factors may be suitable for the present invention.

Figure 9:
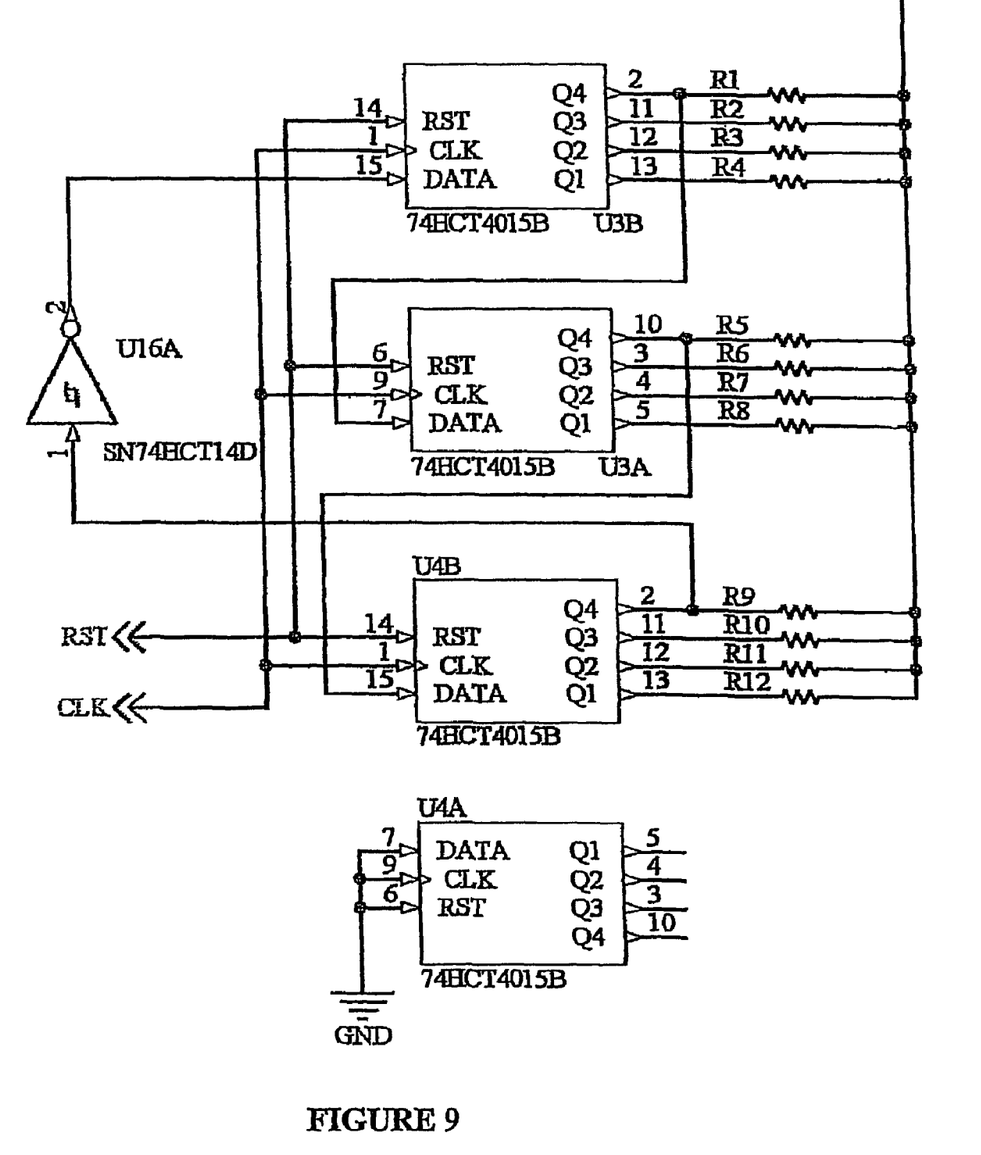
FIG. 9 is an electrical schematic diagram of a pseudo sine wave generator used in a preferred embodiment of the present invention.

We turn now to a detailed description of a particularly preferred embodiment of the present invention, as illustrated in FIGS. 9-15. A pseudo sine wave generator is shown in FIG. 9. This is the first part of the current source illustrated as block 12 in FIG. 1. The current source must provide a relatively constant output current over a fairly broad frequency range. This is needed so that variations in the output signal with frequency will be due to the resonance of the equivalent RLC sampling circuit (described in more detail below) and not due to fluctuations in the current output of the current source.

It is also desirable to operate using low current levels, preferably in the microamp range. The sample cell is small and larger currents can raise the temperature of the sample and can "cook" the sample in some circumstances. Even currents in the milliamp range may be too high for this application. Current sources are well-known in the art, and it is possible to design a current source with the characteristics needed for this application using widely available components. The circuit blocks shown in FIGS. 9-11 form a current source with the characteristics needed for the present invention. Other designs are possible, and would be well within the knowledge of persons skilled in the art.

The pseudo sine wave generator shown in FIG. 9 uses three, identical shift registers (U3B, U3A, and U4B in FIG. 9) with weighted and summed outputs. A TTL clock input and an inverter (U16A) are used with the shift registers to create a stair-step approximation of a sine wave at $\frac{1}{24}^{th}$ the frequency of the clock input.

In one preferred embodiment, the pseudo sine wave generator uses a Hex Schmitt-Trigger Inverter as the inverter (U16A) shown in FIG. 9. A model SN74HCT14 inverter of this type is available from Texas instruments, and this device has worked well in the circuit. Other inverters would work, too, as this is only a preference and other inverters known in the art would provide the same functionality.

Various shift registers also may be used in the pseudo sine wave generator. In the preferred embodiment shown in FIG. 9, a pair of Dual 4-stage static shift registers, model HCF4015B, available from SGS-Thompson Microelectronics, are used. Because the circuit uses only three shift registers, the fourth one (U4A) is not used. The inputs of the unused shift register (U4A) are all grounded and the outputs are not connected to anything.

The schematic configuration of the pseudo sine wave generator shown in FIG. 9 is known in the art. The four outputs of each register are weighted using resistors (R1 through R12) and all the outputs are summed. The data input to each of the three shift registers is provided from one of the outputs of another register, with one such output being inverted before being supplied to the data input. In this manner, a stair-stepped approximation of a sine wave is produced. In a preferred embodiment, the weighting resistors have the values shown in table T-1, below.

TABLE T-1

| | |
|---|---|
| R1 | 165 KΩ |
| R2 | 215 KΩ |
| R3 | 340 KΩ |
| R4 | 1 MΩ |
| R5 | 143 KΩ |
| R6 | 133 KΩ |
| R7 | 133 KΩ |
| R8 | 143 KΩ |
| R9 | 1 MΩ |
| R10 | 340 KΩ |
| R11 | 215 KΩ |
| R12 | 165 KΩ |

The pseudo sine wave generator disclosed here is a practical method of obtaining the desired output. It is relatively simple to construct and does not require programming. An alternative that may be preferable if the system is developed in larger numbers would be use of a uprocessor and ROM lookup table to create the desired output. This alternative approach may allow for lower cost, and easier fabrication in larger quantities than the pseudo sine wave generator configuration discussed above. The use of a uprocessor and lookup table design is well-known in the art and may well be preferred for marketable versions of the invention.

Figure 10:
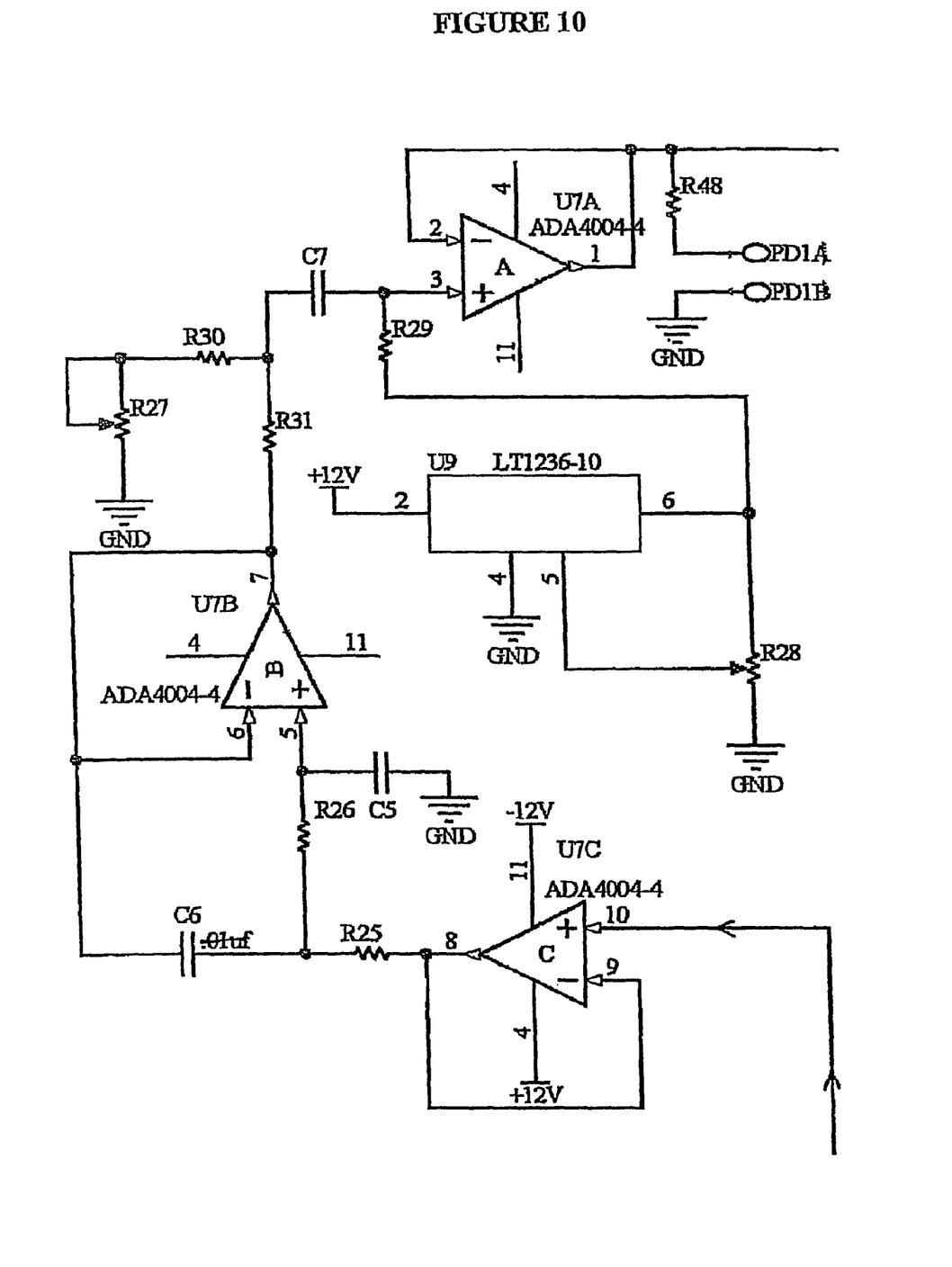
FIG. 10 is an electrical schematic diagram of a low pass filter used in a preferred embodiment of the present invention.

The stair-step sine wave approximation generated by the pseudo sine wave generator is then supplied to a low pass filter that smoothes the wave into a more pure sine wave. FIG. 10 shows such a filter, as used in a preferred embodiment. The filter includes three operational amplifiers in series, with the second one performing the primary filtering operation. The first op amp (U7C) is a buffer. The second op amp (U7B) is operated as a low-pass, Sallen-Key filter, using the filtering capacitors C5 and C6. The amplitude of the sine wave may be varied using potentiometer R27, which is connected to the output of the second op amp (U7B). A DC blocking capacitor C7 is used in the line between the second op amp (U7B) and the third op amp (U7A). A voltage reference U9 is connected to input of the third op amp (U7A). The average value of the sine wave may be varied using the voltage reference U9 and potentiometer R28. A pair of sampling outputs (PD1A and PD1B) are provided at the output of the filter. This allows the sine wave output to be monitored as it is varied in amplitude (i.e., via R27) or average value (i.e., via R28).

The op amps used in the filter shown in FIG. 10 are model ADA4004-4, precision quad amplifiers, available from Analog Devices. Other op amps would work, too, and it is believed that a number of different models would provide the functionality required. The ADA4004-4 is a good product, and seems to work well in this apparatus. The same op amp is used in various other parts of the apparatus, as will be described below.

The voltage reference U9 shown in FIG. 10 is an LT1236 Precision Reference, available from Linear Technology. This device provides a stable output voltage across a range of currents, and allows for adjustment of the average sine wave value by use in combination with potentiometer R28. The final op U7A serves as a buffer.

Figure 11:
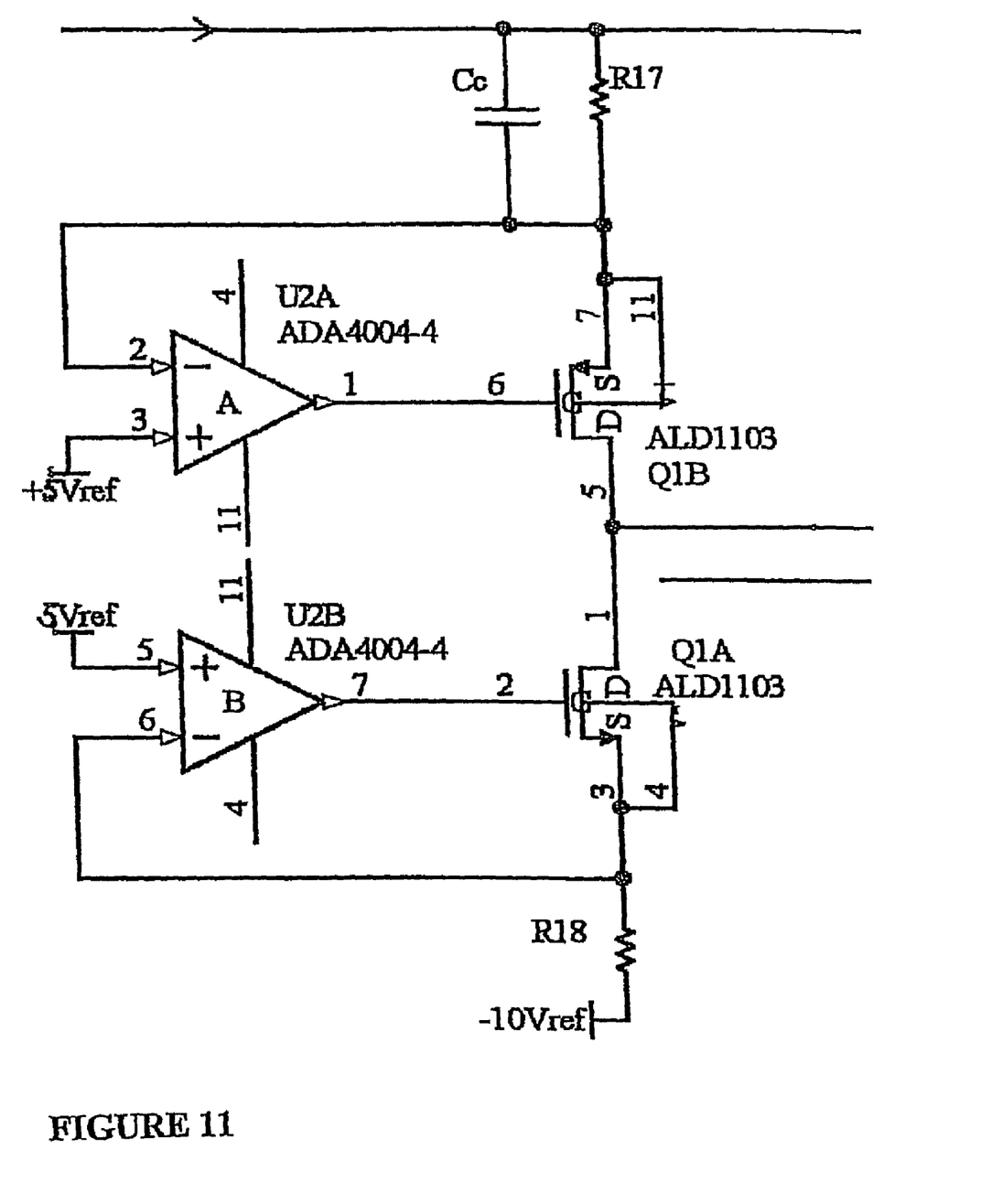
FIG. 11 is an electrical schematic diagram of a transconductor voltage to current source used in a preferred embodiment of the present invention.

The pseudo sine wave generator (shown in FIG. 9) and the low-pass filter (shown in FIG. 10) form the first two parts of the variable frequency current source illustrated as block 12 in FIG. 1. The output of the filter is a smoothed, variable-frequency sine wave. The signal at this point, however, is a voltage signal, and a current source is needed. FIG. 11 shows a transconductor circuit, which effectively converts the voltage sine wave input into a current sine wave output. In order to maximize the isolation of the sampling circuit—that is, to minimize the impedance effects other parts of the circuit have on the sampling circuit—it is desirable to provide a current source having a very high output impedance. The transconductor circuit shown in FIG. 11 provides this result.

The input to the transconductor, the smoothed voltage sine wave from the low-pass filter, is supplied through a capacitor $C_C$ and resistor R17 connected in parallel. The voltage sine wave is then supplied to the inverting input of a first op amp U2A. The noninverting input of this op amp U2A is connected to a +5V reference. The noninverting input of an identical, second op amp U2B is connected to a −5V reference, and the inverting input of the second op amp U2B is connected to ground through a resistor R18. The same model ADA4004-4 op amps identified above may be used for this purpose.

The outputs of these two op amps are supplied to a dual N-channel and dual P-channel matched MOSFET pair. An ALD1103, available from Advanced Linear Devices, Inc., may be used for this purpose. The MOSFET pair produces a current sine wave output with a very high output impedance. This is the current supplied to the sampling circuit.

The frequency is controlled by varying the TTL clock frequency supplied to the pseudo sine wave generator. The sine wave is smoothed by the filter, where the sine wave amplitude and average value may be measured and adjusted. The excitation voltage is converted by the transconductor into an excitation current having very high output impedance. These three circuit blocks form a variable frequency, high output impedance current source.

Other current sources having the required characteristics are known in the art and may be substituted for the specific designs described above. The circuit blocks described above, or others providing comparable functionality, are relatively inexpensive and simple to construct. It is believed that constructing a custom current source (i.e., along the lines described above) is desirable because the current source may be built as a part of a unitary apparatus including the current source, the sampling circuit, and the signal detection and amplification circuits all in a single package. It is also believed, however, that "off-the-shelf" current sources are available and known in the art that may be suitable as plug-ins for the present invention. A variable frequency, high output impedance current source is essential to the present invention, but the particular design described above is only one of a great many possible designs for such a source, as is well understood in the art.

Figure 12:
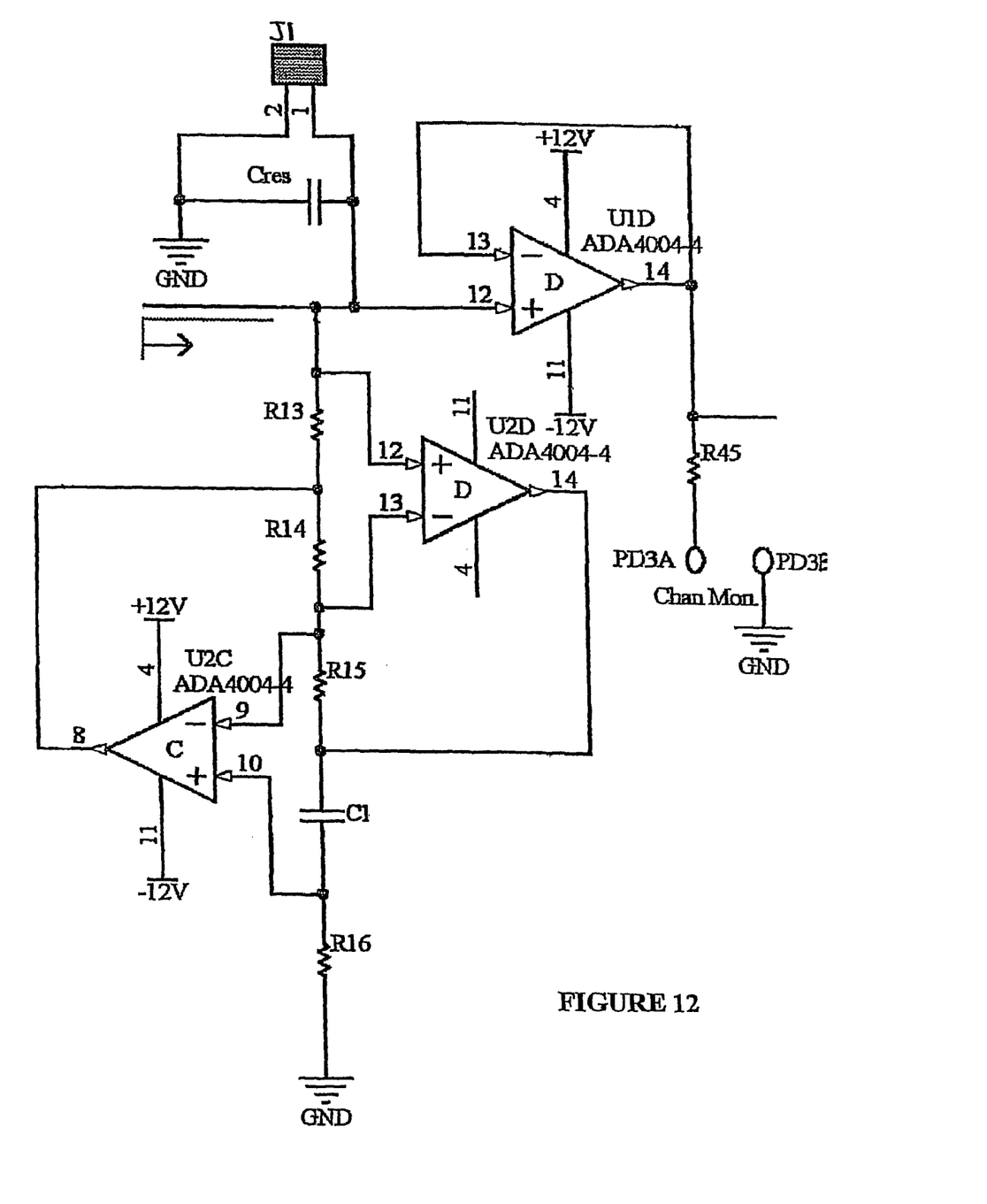
FIG. 12 is an electrical schematic diagram of a sample cell, simulated inductor, and output buffer used in a preferred embodiment of the present invention.

FIG. 12 shows a schematic of a preferred embodiment of the sampling circuit. The sample cell J1 is supplied with the excitation current from the current source. The effective capacitance of the sample cell components is shown as a parallel capacitance $C_{RES}$. A gyrator circuit is shown connected in parallel with the sample cell J1 and the parallel capacitance $C_{RES}$. The gyrator is of the same design as that shown in FIG. 8 and described above. The op amps used in the gyrator (U2D and U2C) may be ADA4004-4 models, though numerous other op amps would work, too.

In a preferred embodiment, the resistors in the gyrator circuit (R13, R14, R15, and R16) are 33KΩ, and the capacitor (C1) has a value of 120 pF. The effective impedance of a gyrator using these components is approximately 130.7 mH. The gyrator, therefore, simulates a relatively large inductor connected in parallel with the resistance of the sample cell J1 and the parallel capacitance $C_{RES}$. This forms an equivalent parallel RLC circuit. By operating this circuit at its resonance frequency, the capacitive and inductive impedances cancel out, leaving only the resistance of the sample cell J1.

If the parallel cell capacitance $C_p$ is approximately 100 pF, and the effective inductance exhibited by the gyrator is approximately 130.7 mH, then the resonance frequency of the equivalent parallel RLC circuit is in the desired range. It is desirable to operate within the range of 10-100 kHz, and these values place the resonance frequency within that range. The frequency range is determined in large part by the range at which the current source will operate with a constant, or nearly constant, current output. The current source disclosed herein provides that functionality, while also producing a low current level, as explained above. It is important to obtain a resonance frequency within this range, because the resonance frequency is not calculated mathematically in practice—it cannot be, as the capacitance of the sample cell cannot be measured in practice—but is determined empirically by sweeping the frequency of the current source until a maximum output signal is achieved. The calculation performed here is based on a very rough approximation of the sample cell capacitance in order to determine whether the frequency falls within a generally acceptable range. So long as the resonance frequency is between approximately 1 kHz and 1 MHz, the apparatus should work as intended. Even higher or lower resonance frequencies should work. If, however, it is found that the resonance frequency is higher or lower than desired, a different resonance frequency may be obtained by using a different size capacitor in the gyrator circuit. It is expected that a capacitor in the general range of 100-200 pF will work well for the present invention.

The output of the equivalent parallel RLC circuit is supplied to a buffer amplifier U1D, which may be a model ADA4004-4 or other, general purpose op amp. A buffer is used here for its high input impedance, which tends to isolate the equivalent RLC circuit from the impedance of other parts of the apparatus. The output of the sampling circuit may be measured using sample connections PD3A and PD3B, as shown in FIG. 12.

Figure 13:
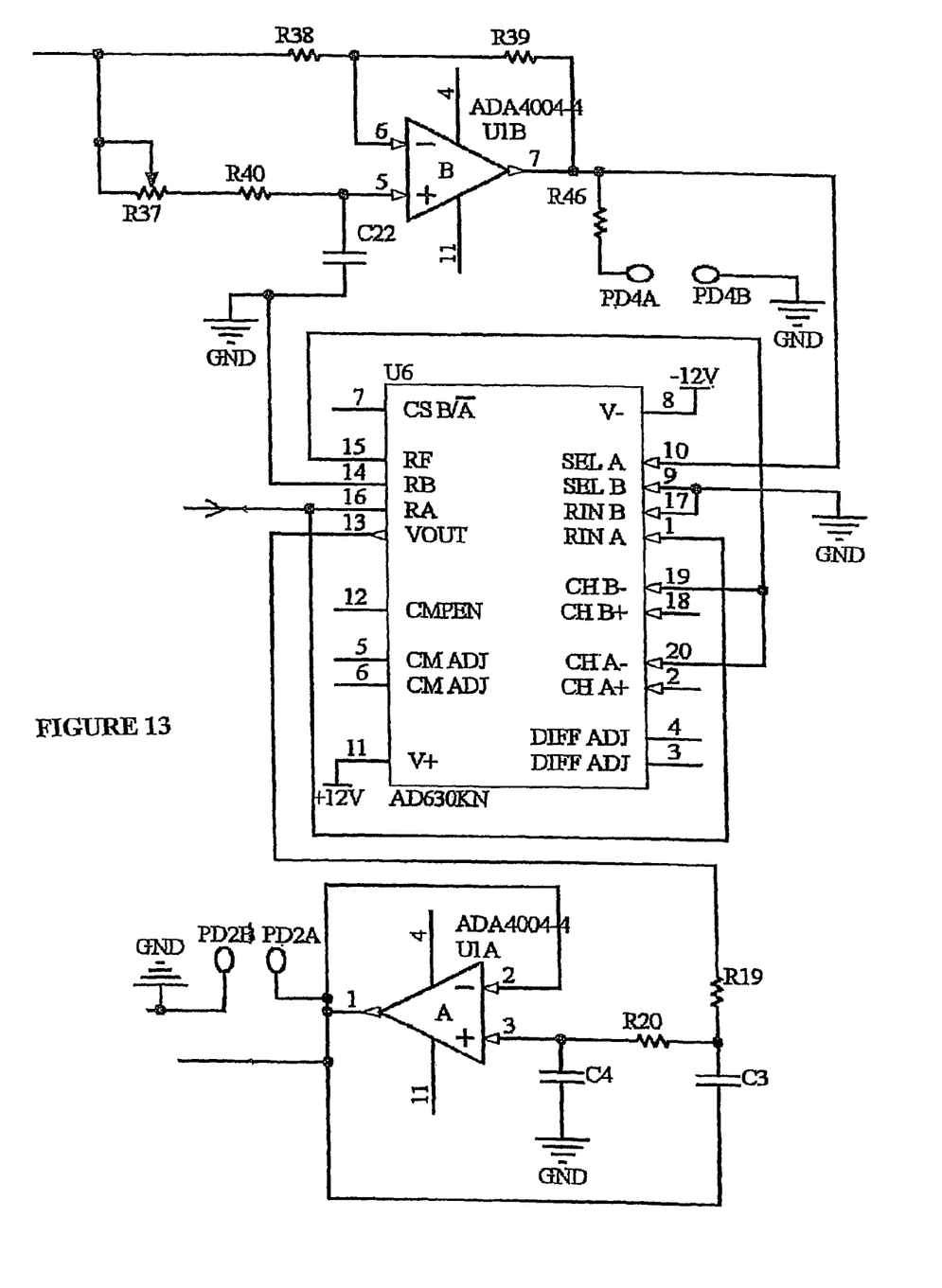
FIG. 13 is an electrical schematic diagram of a phase sensitive detector and filter used in a preferred embodiment of the present invention.

When the circuit is operated at the resonance frequency of the equivalent parallel RLC sampling circuit, the output of that circuit should be phase shifted by 0° relative to the input to the sampling circuit. This phase shift is detected using a phase sensitive detector U6, as shown in FIG. 13. The output of the low-pass filter used in the current source (i.e., the smoothed voltage sine wave) is also supplied to the phase sensitive detector U6 as a reference, so that the signal from the sampling circuit can be synchronously detected. In addition, a phase shift circuit is provided that allows the phase of the reference signal (i.e., the smoothed voltage sine wave) to be shifted by up to −83°. This is accomplished by an op amp U1B (another ADA4004-4 may be used here) with a phase adjustment potentiometer R37 connected to its noninverting input. Measurement terminals (PD4A and PD4B) may be provided to monitor adjustments to the phase of the reference signal. In the preferred embodiment shown in FIG. 13, the phase sensitive detector is a balanced modulator/demodulator, model AD630, available from Analog Devices.

The output of the phase sensitive detector is a voltage signal proportional to the phase difference between the reference and the output of the sampling circuit. The amplitude of the signal also will be proportional to the resistance of the sample cell. This output signal is supplied to a Sallen-Key low-pass filter consisting of an op amp U1A and filtering capacitors C3 and C4. A pair of sampling contacts (PD2B and PD2A) may be provided at the output of this filter.

The operation of the invention may now be understood. The excitation sine wave is adjusted, as necessary, for amplitude and average value. The sample contacts in the current source low-pass filter facilitate such adjustments. The output of the phase sensitive detector (i.e. the detector U6 and the low-pass filter, in combination) is then monitored as the frequency of the current source is swept through the general range in which the resonance frequency is expected to be. When the output of the phase sensitive detector is at its maximum, the resonance frequency has been found. The frequency of the current source is then set and remains stable throughout the rest of the operations.

Though the phase shift due to the equivalent RLC circuit should be 0° when the circuit is at resonance, the measured phase shift is likely to be somewhat less than 0° in practice. To minimize the actual phase shift between the reference and detected signal, the phase of the reference signal (i.e., the smoothed voltage sine wave) may be adjusted by R37. This adjustment provides a greater signal to noise ratio by ensuring a minimum phase shift between signal and reference as exhibited at the output of the phase sensitive detector.

To further enhance the output signal, it is desirable to null the signal based on all background contributions. This background "noise" is due to a combination of effects, including the physical components of the sample cell, other circuit components, and the resistance of the buffer solution in the sample cell. The buffer solution resistance is typically the largest contributor to this background "noise." The signal is, in that sense, not really noise because the buffer solution is the actual sample being measured. It is, nevertheless, desirable to null out the part of the output signal caused by all background sources, including the buffer solution, so that the output signal will be proportional only to perturbations in the resistance of the sample solution. That is, the desired result is an output signal directly proportional to conductivity changes in the sample cell caused when items of interest pass the electrodes.

Figure 14:
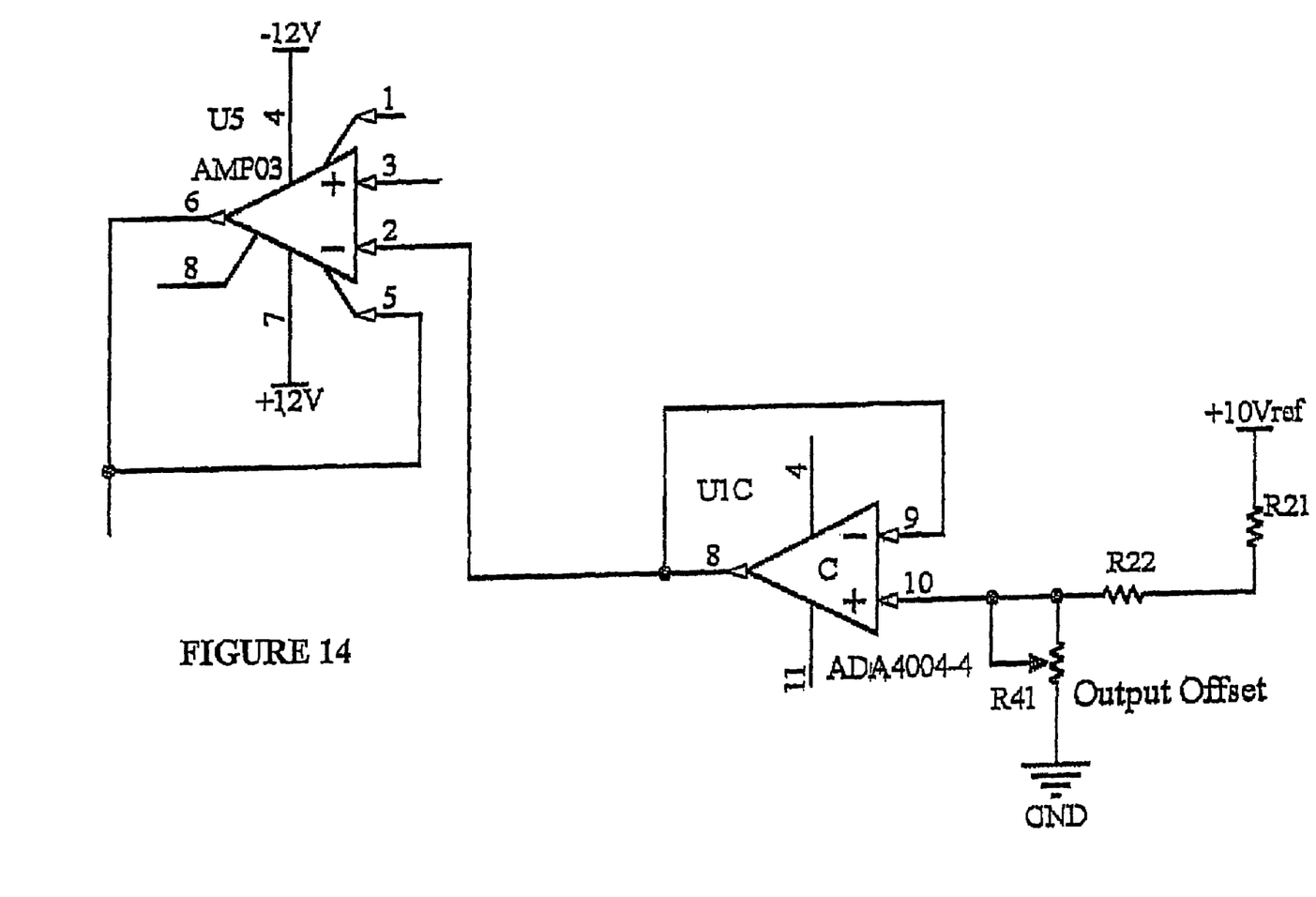
FIG. 14 is an electrical schematic diagram of a background conductivity offset circuit and a differencing amplifier used in a preferred embodiment of the present invention.

By isolating the output signal to only that caused by items of interest, it is possible to employ a high-gain output amplifier, which further enhances the performance of the system. The output signal due to the background components would often saturate such an amplifier, so these components must be removed if such an amplifier is to be employed. This result is obtained through use of a background conductivity offset circuit and a differencing amplifier, as shown in FIG. 14.

The output of the phase sensitive detector and low-pass filter combination is supplied to the noninverting input of a differencing amplifier U5. An AMP03 differential amplifier, available from Analog Devices (or the equivalent INA133 from Texas Instruments), works well for this application, though other differencing op amps should also work. A background conductivity offset circuit supplies the signal to the inverting input of the differencing amplifier U5. The background conductivity offset circuit consists of a voltage divider with an adjustment potentiometer R41 connected through a buffer amplifier U1C (an ADA4004-4 or other general purpose op amp may be used here). Once the circuit adjustments described above have been performed, the output of the phase sensitive detector and band-pass filter combination will be due to the background factors described above. No samples of interest have been supplied to the sample cell at this point. The output of the differencing amplifier U5 is now monitored, and the potentiometer R41 is adjusted until that output is zero. The output is thus nulled, and all background contributions are removed.

Figure 15:
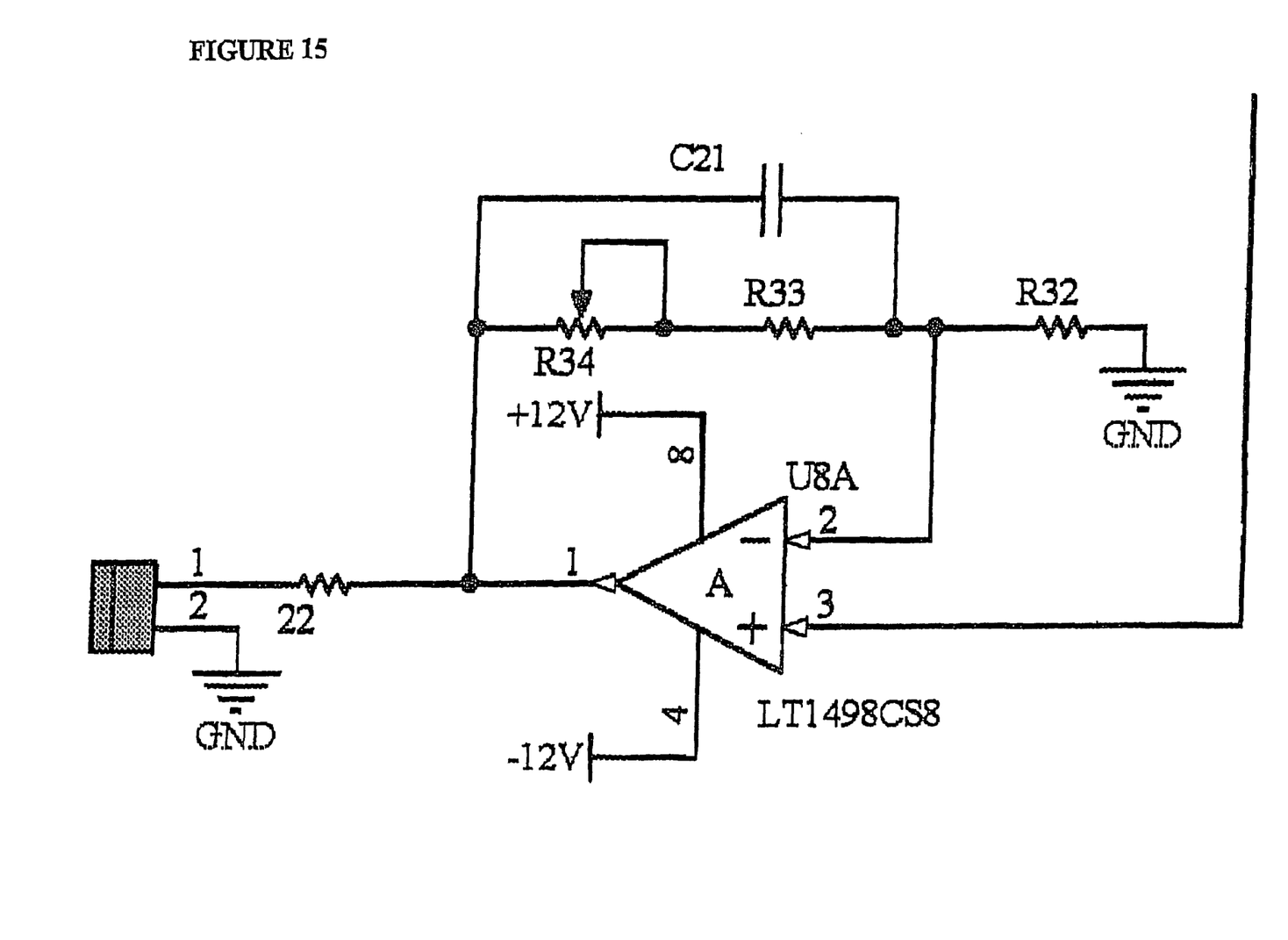
FIG. 15 is an electrical schematic diagram of a high-gain output amplifier used in a preferred embodiment of the present invention.

The output of the differencing amplifier U5 is supplied to a high-gain output amplifier, as shown in FIG. 15. An LT1498 op amp, available from Linear Technology, may be used, though other high-gain op amps would also work. The gain may be set using potentiometer R34. The output of the high-gain output amplifier is supplied to a signal processing system (shown schematically as J2 in FIG. 15) or other suitable device to display, record, or analyze the results. The signals shown in FIG. 7 are illustrative of the type of output signals obtained using the present invention.

Figure 16:
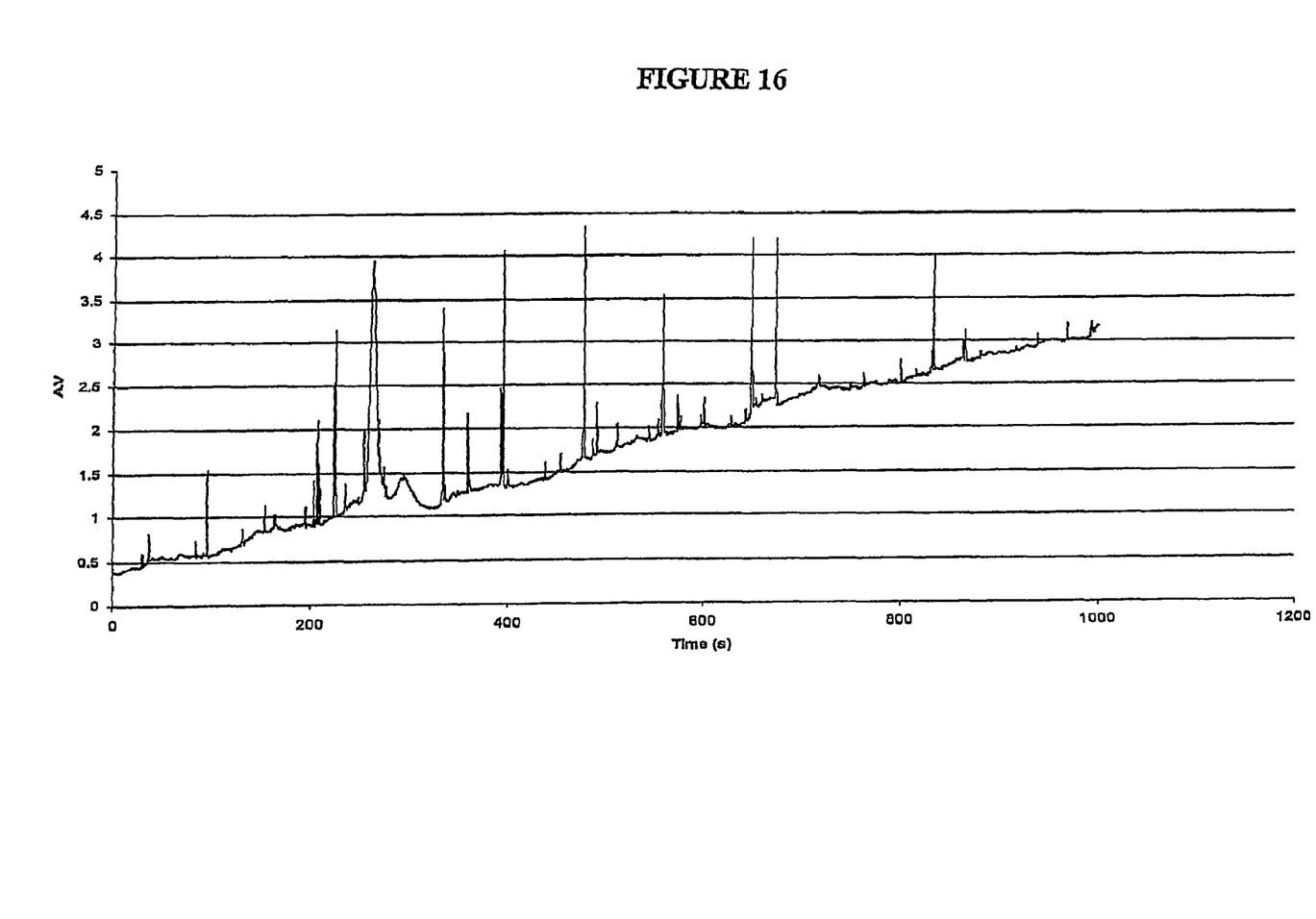
FIG. 16 is a graph showing actual results of a test run using a preferred embodiment of the present invention.

The preferred embodiment of the invention described above works quite well for counting items in a buffer solution. An example of the actual performance of the invention is found in FIG. 16, which shows the output signal over time. In this test, a sample containing 58 cancer cells was used. As each cancer cell passed through the sample cell, a spike was seen in the output signal. The spikes differ in size, but even the small spikes were large enough, relative to the baseline, to allow for accurate detection of the cancer cells. In this run, and in other tests of the present invention, the count obtained using the invention matched exactly with the number of cancer cells known to be in the sample.

While the preceding description is intended to provide an understanding of the present invention, it is to be understood that the present invention is not limited to the disclosed embodiments. To the contrary, the present invention is intended to cover modifications and variations on the structure and methods described above and all other equivalent arrangements that are within the scope and spirit of the claims.

I claim:

1. A conductivity measuring apparatus, comprising:
   a. a variable frequency, high output impedance, current source;
   b. a sample cell having both resistive and capacitive characteristics electrically connected to the current source;
   c. a low-loss, low-noise inductance connected to the current source and in parallel with the sample cell, such that the sample cell and inductance effectively form a parallel RLC circuit;
   d. a high input impedance buffer amplifier connected to the output of the parallel RLC circuit;
   e. a phase sensitive detector connected to the output of the high input impedance buffer amplifier;
   f. a background conductivity offset circuit;
   g. a differencing amplifier with a first input connected to the output of the phase sensitive detector and a second input connected to the output of the background conductivity offset circuit; and
   h. a high gain output amplifier connected to the output of the differencing amplifier.

2. The apparatus of claim 1, wherein the sample cell further comprises a fluid tube through which a sample fluid may be passed, a pair of electrodes positioned on opposite sides of the fluid tube, such that the cell may be electrically modeled as a resistor in parallel with a capacitor.

3. The apparatus of claim 1, wherein the sample cell is formed as part of an integrated circuit having conductive polymer electrodes.

4. The apparatus of claim 1, wherein the sample cell further comprises a cylindrical tube having a diameter of approximately 50 microns and a pair of electrodes positioned on opposite sides of the tube, the electrodes being approximately 75 microns in length.

5. The apparatus of claim 1, wherein the low-loss, low-noise inductance is an inductor.

6. The apparatus of claim 1, wherein the low-loss, low-noise inductance is a gyrator circuit that simulates an inductor.

7. The apparatus of claim 1, wherein the frequency of the variable frequency, high output impedance, current source is set to the resonance frequency of the parallel RLC circuit formed by the sample cell and the low-loss, low-noise inductance.

8. The apparatus of claim 1, wherein the phase sensitive detector is configured to detect a phase shift between the input and output of the parallel RLC circuit formed by the sample cell and the low-loss, low-noise inductance.

9. The apparatus of claim 1, wherein the phase sensitive detector further comprises a phase shift detector and a band-pass filter.

10. The apparatus of claim 1, wherein the background conductivity offset circuit is adjusted so that the output of the differencing amplifier is approximately zero when only a buffer solution is present in the sample cell.

11. The apparatus of claim 1, wherein an output of the high gain output amplifier is connected to a signal processing device.

12. The apparatus of claim 1, wherein the variable frequency, high output impedance current source further comprises a pseudo sine wave generator, a low pass filter, and a transconductor.

13. The apparatus of claim 12, wherein the pseudo sine wave generator further comprises a TLL clock connected to an input of each one of a plurality of shift registers, an inverter connected to an output of one shift register and to a data input of another shift register, and weighting resistors connected to outputs of the shift registers.

14. The apparatus of claim 12, wherein the low pass filter further comprises a plurality of operational amplifiers connected in series, a DC blocking capacitor, a sine wave amplitude adjustment potentiometer, and a voltage reference connected to a sine wave average adjustment potentiometer and to the input of the final operational amplifier in the filter.

15. The apparatus of claim 12, wherein the transconductor further comprises a pair of operational amplifiers, each operational amplifier connected to one of a matched pair of MOSFETs, such that a voltage excitation entering the transconductor is converted to a current excitation with a high output impedance, which is then supplied to the sample cell and inductance.

16. A conductivity measuring apparatus, comprising:
   a. a variable frequency current source;
   b. a sample cell electrically connected to the current source via two electrodes; wherein the sample cell comprises a cylindrical fluid tube through which a sample fluid may be passed; wherein the two electrodes are positioned on opposite sides of the cylindrical fluid tube; and wherein the cylindrical fluid tube has a diameter less than 100 microns;
   c. an inductance electrically connected to the current source and in parallel with the sample cell, such that the sample cell and the inductance form the electrical equivalent of a parallel RLC circuit; and
   d. a detector electrically connected to the sample cell wherein:
   e. said apparatus possesses sufficient sensitivity to be able to accurately detect the presence of an individual cell in a buffer solution.

17. The apparatus of claim 16, wherein the current source further comprises a pseudo sine wave generator, a low pass filter, and a transconductor.

18. The apparatus of claim 16, wherein the inductance is a gyrator.

19. The apparatus of claim 16, wherein the sample cell is formed as part of an integrated circuit.

20. The apparatus of claim 16, wherein the cylindrical tube has a diameter of approximately 50 microns, and each of the electrodes is approximately 75 microns in length.

21. The apparatus of claim 16, wherein the electrical equivalent of a parallel RLC circuit has a resonance frequency within the range of 1 kHz to 1 MHZ.

22. The apparatus of claim 21, wherein the variable frequency current source is tuned to the resonance frequency of the electrical equivalent of a parallel RLC circuit.

23. The apparatus of claim 22, wherein the detector is nulled to an approximately zero output with a buffer solution in the sample cell.

* * * * *